US012383699B2

(12) United States Patent
Schierholz

(10) Patent No.: US 12,383,699 B2
(45) Date of Patent: Aug. 12, 2025

(54) CATHETER ATTACHMENT MADE OF PLASTIC THAT CONTAINS MOLECULARLY DISPERSED POLYCHLORINATED PHENOXYPHENOL (PCPP)

(71) Applicant: Jörg Michael Schierholz, Starnberg-Bete (DE)

(72) Inventor: Jörg Michael Schierholz, Starnberg-Bete (DE)

(73) Assignee: Jörg Schierholz, Starnberg-Bete (DE)

( * ) Notice: Subject to any disclaimer, the term of this patent is extended or adjusted under 35 U.S.C. 154(b) by 0 days.

(21) Appl. No.: 16/481,869

(22) PCT Filed: Jan. 31, 2018

(86) PCT No.: PCT/EP2018/052381
§ 371 (c)(1),
(2) Date: Jul. 30, 2019

(87) PCT Pub. No.: WO2018/141783
PCT Pub. Date: Aug. 9, 2018

(65) Prior Publication Data
US 2019/0374744 A1 Dec. 12, 2019

(30) Foreign Application Priority Data
Jan. 31, 2017 (EP) ..................................... 17154003

(51) Int. Cl.
*A61M 25/00* (2006.01)
*A61L 29/16* (2006.01)

(52) U.S. Cl.
CPC .... *A61M 25/0009* (2013.01); *A61M 25/0043* (2013.01); *A61M 25/0097* (2013.01); *A61L 29/16* (2013.01); *A61L 2300/202* (2013.01); *A61L 2300/404* (2013.01); *A61M 2025/0056* (2013.01)

(58) Field of Classification Search
None
See application file for complete search history.

(56) References Cited

U.S. PATENT DOCUMENTS

| | | | |
|---|---|---|---|
| 6,575,959 B1* | 6/2003 | Sarge | A61M 25/0014 604/533 |
| 2004/0249441 A1* | 12/2004 | Miller | A61L 31/16 623/1.42 |
| 2011/0301553 A1* | 12/2011 | Goral | A61L 29/085 604/265 |
| 2013/0274686 A1* | 10/2013 | Ziebol | A61L 2/186 604/265 |

FOREIGN PATENT DOCUMENTS

| | | | |
|---|---|---|---|
| WO | 02-066595 A1 | | 8/2002 |
| WO | WO 2003066119 | * | 8/2003 |
| WO | 2006-032904 A2 | | 3/2006 |

OTHER PUBLICATIONS

Chegg. Structure of Dacron. Retrieved (Year: 2021).*
International Search Report for Application No. PCT/EP2018/052381 dated Apr. 19, 2018.
Junker et al., "Effects of triclosan incorporation into ABS plastic on biofilm communities", Journal of Antimicrobial Chemotherapy 53, p. 989-996, (2004).
Maki et al., "The Risk of Bloodstream Infection in Adults With Different Intravascular Devices: A Systematic Review of 200 Published Prospective Studies", Mayo Clin Proc.;81(9):1159-1171, (2006).
Russell et al., "Whither triclosan?", Journal of Antimicrobial Chemotherapy 53, p. 693-695, (2004).
Schierholz et al., "Schwierige Suche nach neuen Werkstoffen", A-1006 (26) Deutsches Ärzteblatt 95, Heft 17, (Apr. 24, 1998).
Simon et al., "Healthcare-associated infections in pediatric cancer patients: results of a prospective surveillance study from university hospitals in Germany and Switzerland", BMC Infectious Diseases, 8:70, (2008).
Sitges-Serra et al., "Cather Sepsis: The Clue is the Hub", Surgery, vol. 97, No. 3, p. 355-357, (1985).
Fisher, "Development And Evaluation of an Antimicrobial Urinary Catheter", University of Nottingham, p. 1-281, (2011).

* cited by examiner

*Primary Examiner* — David J Blanchard
*Assistant Examiner* — Sarah J Chickos
(74) *Attorney, Agent, or Firm* — Christensen, Fonder, Dardi PLLC; Peter S. Dardi

(57) ABSTRACT

The invention relates to a catheter attachment made of a non-elastomeric plastic that contains homogeneously distributed, molecularly dispersed polychlorinated phenoxyphenol (PCPP), in particular 5-chloro-2-(2,4-dichloro-phenoxy)-phenol (Irgasan©).

11 Claims, 2 Drawing Sheets

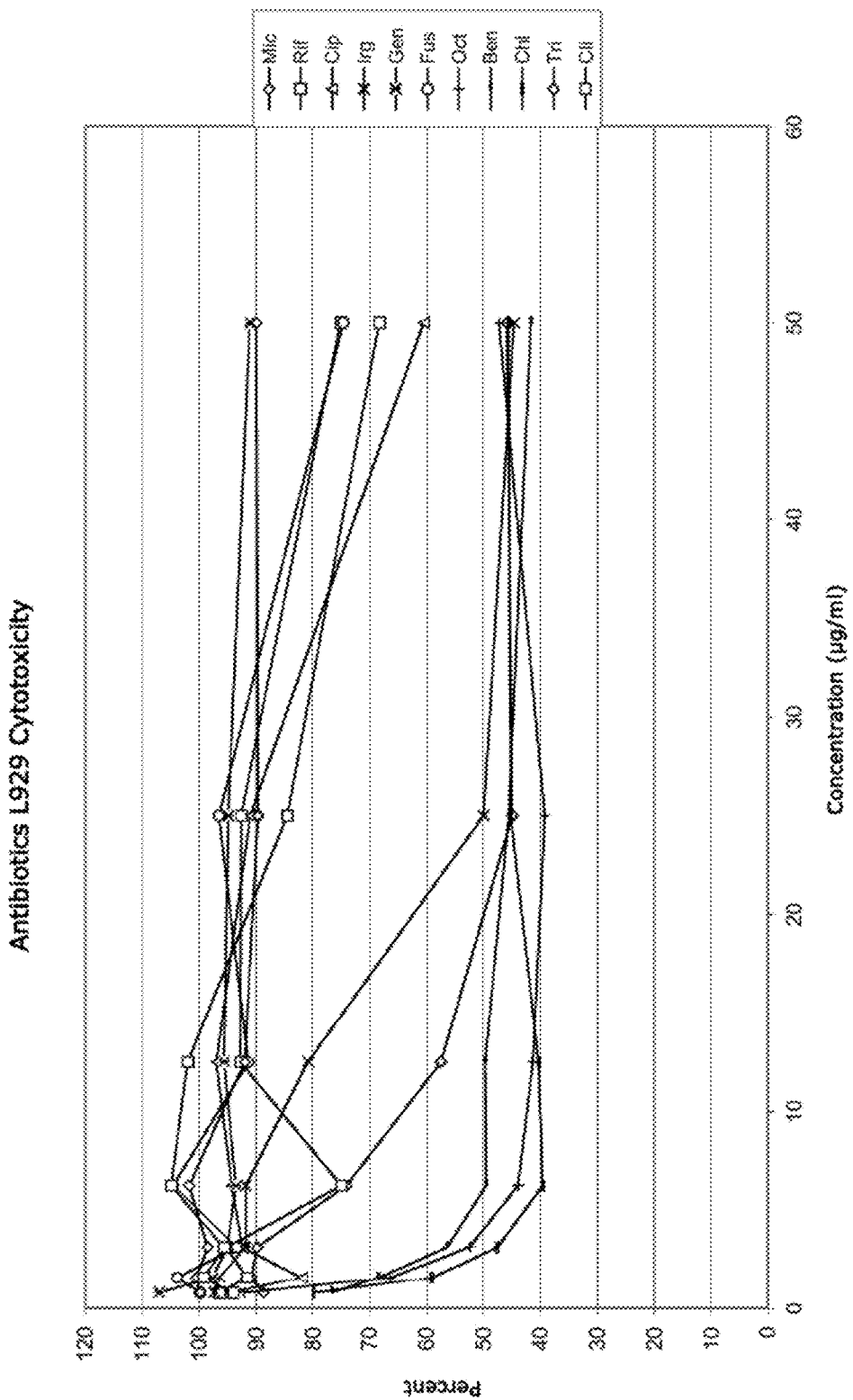

CATHETER ATTACHMENT MADE OF PLASTIC THAT CONTAINS MOLECULARLY DISPERSED POLYCHLORINATED PHENOXYPHENOL (PCPP)

This application is a National Stage filing of PCT Application No.: PCT/EP2018052381, filed Jan. 31, 2018, which claims priority to European Patent Application No.: 17154003.2, filed Jan. 31, 2017, both of which are hereby incorporated herein by reference.

TECHNICAL FIELD

The present invention relates to a catheter attachment made of a non-elastomeric plastic comprising molecularly dispersed polychlorinated phenoxyphenol (PCPP).

BACKGROUND

Infusions through central and peripheral catheters are fundamental components of intensive care and of the (perioperative) management of severely ill patients. Parenteral nutrition, volume replacement, hemodynamic monitoring and the usually continuous medicament dosage represent the most important indications (Schierholz, M., Rump, A. F. E., Pulverer, G., Kathetermaterialien: Schwierige Suche nach neuen Werkstoffen, Deutsches Ärzteblatt 95(17), A1007-1009, (1998)). The dimension of the increasing problems of nosocomial catheter-associated infections can be illustrated by a few numbers: For almost 30 million central venous catheters (CVCs) implanted annually in the U.S. alone, the rate of catheter-associated sepsis is 2.8% to 10% of all intensive care patients (D. Maki et al., The risk of bloodstream infection in adults with different intravascular devices: A systematic review of 200 published prospective studies, Mayo Clin Proc. 81(9): 1159-1171, 2006).

INTRODUCTION AND SUMMARY OF THE INVENTION

The lethality rate varies from 4 to 20%, depending on the reference. The severe clinical consequences are followed by economical ones: extension of the intensive care residence time by up to 6.5 days, extension of the period of hospitalization by a total of up to 12.5 days with an additional cost of more than $10,000 (A. Simon et al., Healthcare associated infections in pediatric cancer patients: results of a prospective surveillance study from university hospitals in Germany and Switzerland, BMC Infectious disease, 8: 70-79), 2008). Contaminated catheter hubs, extensions, connectors, adapters, septums, valves, connecting pieces, stopcocks, injection ports, Luer locks, insertable or screwable coupling boxes as well as feed line closures will infect the catheter lumens, and after a few days of dwelling, they become as infection-relevant as the subcutaneous path (Sitges-Serra A, Linares J, Garau J: Catheter sepsis: the clue is the hub. Surgery 97 (1985) 355-357. Schierholz Jörg M, Pulverer Gerhard, Rump Alexis F E: Katheter-Materialien: Schwierige Suche nach neuen Werkstoffen. Dtsch Ärztebl 95 (1998) A1006-A1009). Catheter attachments enable medical devices to be connected at the proximal end of a catheter flexible tube or at the feed line valve of an in-dwelling peripheral venous cannula for supplying or collecting fluids by means of injection, infusion or transfusion, for which purpose insertable or screwable coupling boxes exist. Attachments can be provided with a closure element (stopcocks).

The same problem exists with contaminated connecting pieces (or spacers) of an inhalative therapy, for example, the medicamentous therapy of COPD and asthma, namely that microbial contaminants can get along into the respiratory tract.

It is the object of the present invention to avoid the above-described drawbacks, and to provide antimicrobially active catheter attachments for the prevention of contaminations and infections.

The object of the invention is achieved by an antimicrobially equipped catheter attachments according to claim 1. The dependent claims relate to particular embodiments of the catheter attachments according to the invention.

In contrast to the medical devices disclosed in WO 2006/032904A2, the catheter attachment according to the invention is not only impregnated with antimicrobially active substance used according to the invention, but the antimicrobially active substance, which is polychlorinated phenoxyphenol, is in a molecularly dispersed state in the non-elastomeric plastic of which the catheter attachment is made according to the invention. It is only because of this feature that the catheter attachment according to the invention can develop its advantageous properties. If the catheter attachment were only impregnated, as would be possible for elastomeric plastics according to the prior art, the catheter attachment would lose most of its antimicrobial effectiveness within a short period of time (burst effect) and lose its mechanical properties, and thus could no longer ensure its function reliably. The molecularly disperse distribution of the antimicrobially active substance is thus a novel and non-obvious approach over the disclosure according to WO 2006/032904A2 in a form-stable non-elastomeric polymer.

WO 02/066595A1 relates to a septum made of an elastomeric plastic, which is not suitable for the formation of a catheter attachment within the meaning of the invention.

The catheter attachment according to the invention is produced from a plastic material comprising homogeneously distributed polychlorinated phenoxyphenol (PCPP), especially 5-chloro-2-(2,4-dichlorophenoxy)phenol (Irgasan). Irgasan is a generally known trade name of 5-chloro-2-(2,4-dichlorophenoxy)phenol.

BRIEF DESCRIPTION OF THE DRAWINGS

FIG. 3 shows results of a fibroblast cytotoxicity test (MTT) with different antimicrobial substances.

DETAILED DESCRIPTION OF THE INVENTION

Figure 1:
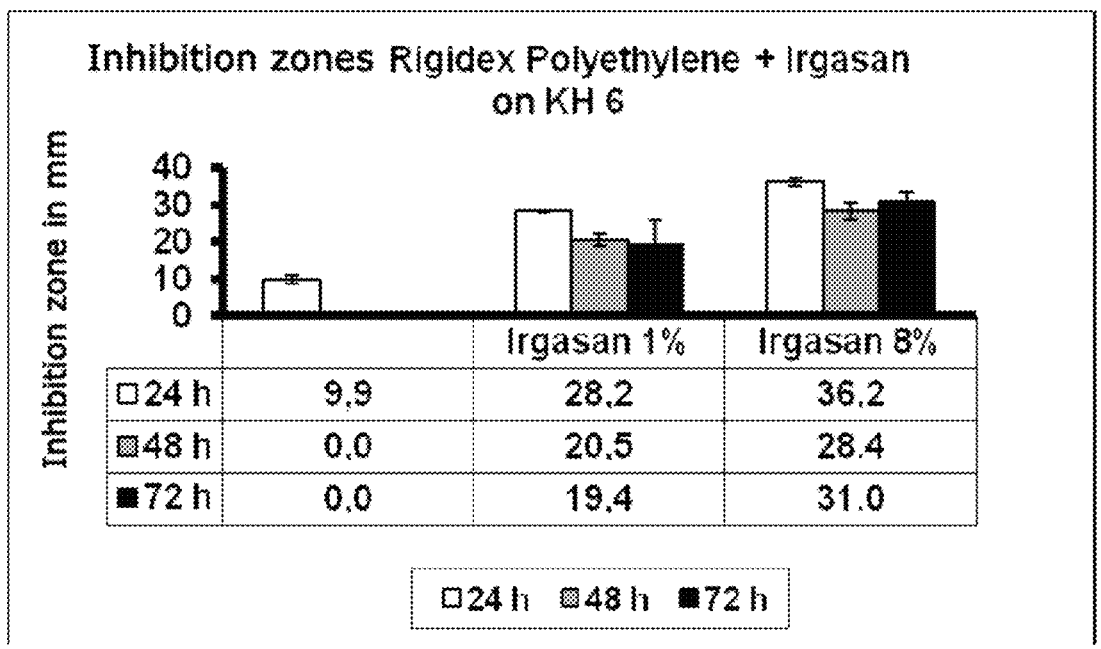
FIG. 1 shows inhibition zones of Rigidex polyethylene+Irgasan on *S. epidermidis* strain KH 6.

The catheter attachment according to the invention comprises molecularly dispersed polychlorinated phenoxyphenol (PCPP), especially 5-chloro-2-(2,4-dichlorophenoxy) phenol. Those skilled in the art understand the term "molecularly dispersed" to mean, inter alia, particle sizes of <1 µm. In the context of the invention, in particular, those skilled in the art understand it to mean polychlorinated phenoxyphenol (PCPP), especially 5-chloro-2-(2,4-dichlorophenoxy)phenol, arranged in a dispersed state in the polymeric material from which the catheter attachment has been formed. The size of the polychlorinated phenoxyphenol (PCPP) particles, especially 5-chloro-2-(2,4-dichlorophenoxy)phenol particles, is a size resulting in a macroscopically homogeneous material. In particular, the size of the particles in the polymeric material is smaller than 10 nm, especially smaller than 1 nm. Molecularly dispersed systems are clear and transparent solutions in which no phase boundary can be seen. They are characterized by being physically stable and homogeneous, i.e., the dissolved ions and molecules cannot be separated from the solvent by filtering or centrifuging (true solution). Thus, they differ from substances that are merely colloidally or coarsely dispersed.

Typically, the polychlorinated phenoxyphenol (PCPP), especially 5-chloro-2-(2,4-dichlorophenoxy)phenol, is present in an amount of at least 0.01% by weight, especially 0.05% by weight to 10% by weight, in the catheter attachment, based on the weight of the catheter attachment.

Plastics are coarsely divided into elastomers, thermoplasts and thermosets. The plastics employed according to the invention do not belong to the elastomers.

In another embodiment, the plastic of the catheter attachment is selected from the group consisting of non-elastomeric thermoplastic materials. Suitable plastics include, in particular, polycarbonates, non-elastomeric rigid polyurethanes, polyethylenes (preferably HDPE), polypropylenes, polybutadienes, polybutylenes, polyketones, polystyrenes, polysulfones, poly(ethylene terephthalates), polyamides, polyacrylates, PVC, and other polymers used in medical technology for catheter attachments or stopcocks. For example, non-elastomeric plastics have a transition temperature above room temperature (25° C.). Non-elastomeric plastics having a glass transition temperature above the temperature of application are also suitable. For example, they are characterized by higher crystalline proportions in the polymer (example: PE-HD: about 80% crystalline proportion vs. PE-LD: 30%), and are usually dimensionally stable towards application-specific mechanical influences.

Typical embodiments of the catheter attachment according to the invention include the following: plugs, connectors, connecting pieces, stopcocks, feed line valves, catheter hubs, extensions, adapters, septums, valves, stopcocks, injection ports, insertable or screwable coupling boxes, and Luer locks.

The products according to the invention are equipped with molecularly dispersed antimicrobial substances, wherein the combinations of polymer with PCPP are balanced by means of similar solubility parameters (cohesion energy densities) that the mechanical properties of the materials are not affected, and in addition an antimicrobial effect is present over an extended period of time. At the same time, the active substances and the injection molding/extrusion methods are coordinated in such a way that the thermostable active substances do not bleed from the catheter attachment materials, and in addition, that the products can be sterilized and at the same time do not have any relevant toxicity. In addition, the PCPPs should have a melting point below the melting point of the thermoplastically processed material, in order that dissolution is successful in the melt, and at the same time be temperature-stable. The invention for the first time provides antimicrobial attachment materials for infusion therapy that have extremely lipophilic chlorinated bisphenols incorporated in the entire attachment material in a molecularly dispersed state. In contrast to elastomeric thermoplasts, it is significantly more difficult with non-elastomeric thermoplasts, which are the support material of attachments, to create sustained release systems having a long antimicrobial effectiveness because of the higher crystallinity in the plastic and thus the slower diffusion rate of a physically integrated substance. This applies, in particular, to superficial coatings of attachment materials, because the active substances elute relatively quickly in a coated layer, and such thin layers are mostly not mechanically stable.

The injection of the catheter attachment comprising an active substance onto the edge of a flexible tube or the plastic base of an in-dwelling peripheral venous cannula is most successful on other plastics having a similar cohesion energy density (solubility parameter), because otherwise cracking and disaggregation, i.e., cleft or crack formations are possible on the phase boundary between the two plastics. The molecularly dispersed distribution of the active substance in the blend provides for smooth homogeneous intermediate phases to be formed in the thermoplastic contact sites between the antimicrobial blend and the injection-molded plastic surface of, for example, a catheter flexible tube that allow for permanent bonding.

The invention also relates to a process for preparing the catheter attachment made of plastic according to the invention, in which pellets of the plastic are brought into intimate contact with the phenoxyphenol (PCPP), especially 5-chloro-2-(2,4-dichlorophenoxy)phenol (Irgasan), to obtain a mixture, followed by melting the mixture and preparing the catheter attachment by extrusion or injection molding.

The mixture is obtained, for example, by coating the pellets with phenoxyphenol (PCPP), especially 5-chloro-2-(2,4-dichlorophenoxy)phenol (Irgasan).

In another embodiment, the mixture can be obtained by mixing the pellets with phenoxyphenol (PCPP), especially 5-chloro-2-(2,4-dichlorophenoxy)phenol (Irgasan).

A process for preparing the catheter attachment according to the invention includes the preparation of a homogeneous melt by previously mixing polymer pellets and phenoxyphenol (PCPP), especially 5-chloro-2-(2,4-dichlorophenoxy)phenol (Irgasan), until a uniform coating of the anti-infection agent on the polymer pellets is reached by heating the blending drum beyond the melting point of phenoxyphenol (PCPP), especially 5-chloro-2-(2,4-dichlorophenoxy)phenol (Irgasan). It is also possible to wet the polymer pellets with 0.1-1% of a polyol or alcohol, whereby the phenoxyphenol (PCPP), especially 5-chloro-2-(2,4-dichlorophenoxy)phenol (Irgasan), when it is admixed later, will adhere better on the polymer pellets and thus a better homogeneity of the polymer melt (for example, in double-screw blending) and thereafter the desired homogeneous molecularly-dispersed distribution after the extrusion/injection molding and thus in the final product, the catheter attachments, are achieved.

The polymer pellets coated with the active substance can be processed, for example, with a Babyplast plasticizing and injection aggregate (Christmann Kunststoffverarbeitung, Gummersbach-Krispe, D E) in a dual-stage piston injection aggregate into the stopcocks (plugs), wherein the plastic granules are liquefied almost exclusively by heat conduction and almost without friction.

DE 10 2008 033 224 A1 describes a thermoplastic material with porous metallic silver agglomerates.

The Utility Model G 93 20 337 U describes the integration of silver chloride in attachment materials, and G 91 00 743 U describes the incorporation of silver chloride into an injection port of an in-dwelling peripheral venous cannula.

DE 33 02 567 A1 discloses the superficial coating of a tube with a metal.

U.S. Pat. No. 5,069,907 describes the incorporation of triclosan into a film of surgical covering materials of flexible polyethylene. Thus, elastomeric thermoplasts, preferably elastic PE, are processed into flexible covering films with an adhesive layer in a blow-film extrusion method, or in a liquid acrylic resin.

US 2007/0299409 A1 discloses the integration of different antimicrobial substances into bio-absorbable polymers.

WO 86/02006 describes the coating of catheter attachments with different antimicrobial substances.

The U.S. Pat. No. 5,856,005 describes the preparation of an antimicrobial non-flammable yarn with chlorinated phenoxy substances, preferably in cellulose acetate.

EP 2 956 510 A1 relates to the incorporation of antimicrobial substances into polymer coatings that are cured with UV light (corresponds to PCT/US 2014/015614).

The U.S. Pat. No. Specification 6,106,505 discloses the impregnation of a synergistic combination of triclosan and chlorohexidine into elastomers by immersion methods.

The U.S. Pat. No. 8,277,826 B2 relates to a method for mixing different antimicrobial substances into resins, with a specific ratio of hydrophilic to hydrophobic monomer proportions of the resin.

It is recommendable to combine the right polymer with the antimicrobial substance 5-chloro-2-(2,4-dichlorophenoxy)phenol to prepare a sustainable microbially active system. With plastics like ABS (acrylonitrile-butadiene-styrene) polymers, too low release rates were achieved because both components were not compatible (Effects of triclosan incorporation into ABS plastic on biofilm communities, Journal of Antimicrobial Chemotherapy (2004) 53, 989-996, DOI: 10,1093/jacidkh196).

Surprisingly, homogeneous polymer blends with sustainable effectiveness could be developed with the preferred antimicrobial agent 5-chloro-2-(2,4-dichlorophenoxy)phenol with the polymers selected according to the invention in an injection-molding and extrusion method for the production of the catheter attachments according to the invention. 5-Chloro-2-(2,4-dichloro-phenoxy)phenol is a substance used in many products, from soaps, deodorants and toys to the decolonization of the patients from MRSA with a 2% aqueous solution (A. D. Russell, Whither triclosan? Journal of Antimicrobial Chemotherapy (2004) 53, 693-695, DOI: 10.1093/jac/dkh171). The activity is bactericidal at higher concentrations with multiple targets in the cytoplasm and on the cell membrane, and bacteriostatic at lower concentrations, which is sufficient in principle for the use of antimicrobial connecting pieces with a good bioavailability. The incorporation is selected in such a way that, on the one hand, a sufficient antimicrobial activity is ensured over an extended period of time, and on the other side, no relevant toxicities and no bleeding of the product occur.

The invention is further illustrated by means of the present Examples.

Example 1

Polyethylene granules (Rigidex) were provided with 1% and 8% Irgasan in a mixer, and blended in a mini-injection molding device (Babyplast plasticizing and injection aggregate (Christmann, Gummersbach-Krispe, D E) to form 2 mm thick disks. The antibacterial inhibition zones were tested after 24, 48 and 72 hours as well as after 144 hours against S. epidermidis strain KH6. After 48 hours, a stable plateau formed with an inhibition zone of about 20 mm (1%), 28-30 mm (8%) up to a tested time of 144 hours (FIG. 1).

Example 2

Polycarbonate (Bayer AG) was provided with 1% and 8% Irgasan in a mixer, and blended in a mini-injection molding device to form 2 mm thick disks. The inhibition zones were tested after 24, 48 and 72 hours as well as after 144 hours. After 48 hours, a stable plateau formed with an inhibition zone of about 18 mm (1%) or 38 mm (8%) up to a tested time of 144 hours.

Example 3

Polyamide was provided with 1% and 8% Irgasan in a mixer, and blended in a mini-injection molding device to form 2 mm thick disks. The inhibition zones were tested after 24, 48 and 72 hours as well as after 144 hours. After 48 hours, a stable plateau formed with an inhibition zone of about 22 mm (1%) or 39 mm (8%) up to a tested time of 144 hours.

Example 4

Bacterial adhesion: 1% polyamide-Irgasan was incubated with an over night culture of S. epidermidis strain KH11 at about $10^{-4}$ CFU in MHB (Müller-Hinton Bouillon) for 1 hour, and then incubated in MHB for 24 hours. Thereupon, the number of adhering CFUs was determined in a direct contact test. Zero colonies was counted.

Example 5

Figure 2:
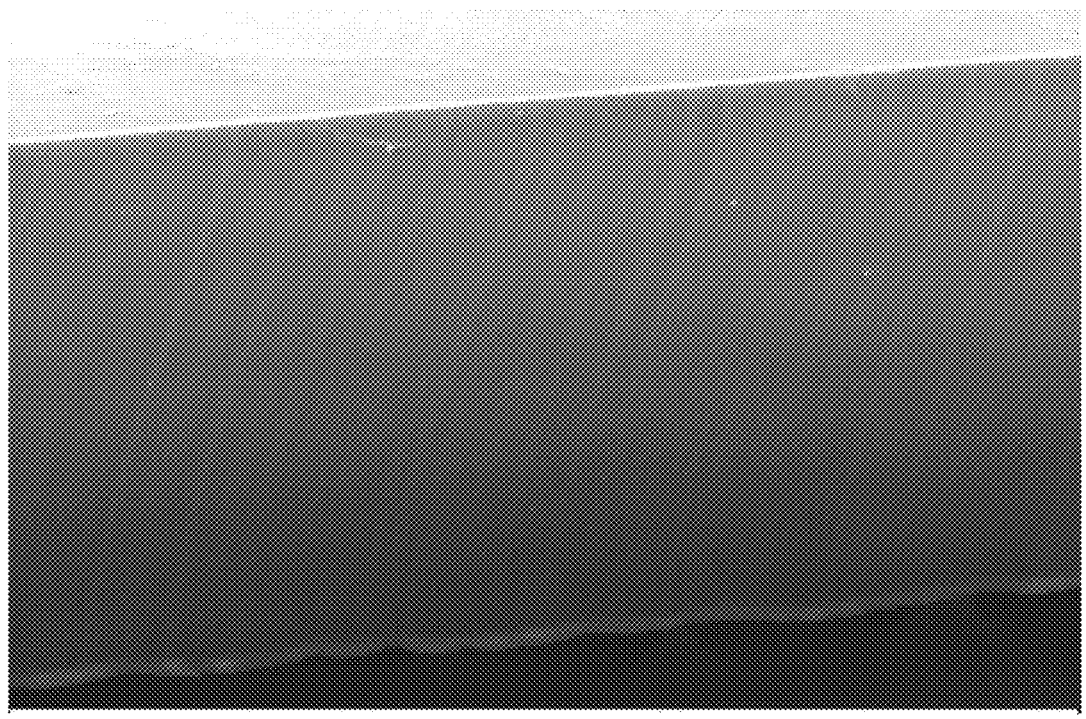
FIG. 2 shows a scanning electron micrograph of the molecularly disperse distribution of 1% Rigidex-Irgasan.

REM images for molecularly-dispersed distribution 1% Rigidex-Irgasan (FIG. 2).

Example 6

The release rates for inhibition zones of about 20 mm were chosen in such a way that only a minimum adverse affection was found in a fibroblast-cytotoxicity test for an Irgasan release ($cm^2$) of 2-4 mg/l (FIG. 3). In FIG. 3, the following meanings apply: Mic: miconazole, Tri: trimetoprim, Rif: rifampicin, Irg: Irgasan, Gen: gentamicin, Fus: fusidic acid, Oct: octenidine, Ben: benzylpenicillin, Chl: chlorohexidine, Cli: clindamycine. FIG. 3 shows that the fibroblasts are hardly inhibited, and the substance is non-toxic, up to a maximum concentration of 10 µg/ml, in contrast to the antiseptics chlorohexidine and octenidine.

The invention claimed is:

1. A catheter attachment consisting of a non-elastomeric thermoplastic material and molecularly homogeneously dispersed polychlorinated phenoxyphenol (PCPP) within the non-elastomeric thermoplastic material, wherein said catheter attachment is selected from the group consisting of stopcocks, feed line valves, catheter hubs, valves, injection ports, and Luer locks.

2. The catheter attachment according to claim 1, wherein said polychlorinated phenoxyphenol (PCPP) is present in an amount of at least 0.05% by weight, based on the weight of the catheter attachment.

3. The catheter attachment according to claim 2, wherein said polychlorinated phenoxyphenol (PCPP) is present in a range of from 0.05% by weight to 10% by weight, based on the weight of the catheter attachment.

4. The catheter attachment of claim 1, wherein the polychlorinated phenoxyphenol is 5-chloro-2-(2,4-dichlorophenoxy)phenol.

5. The catheter attachment according to claim 1, wherein the non-elastomeric thermoplastic material is selected from polycarbonates, non-elastomeric rigid polyurethanes, polyethylenes, polypropylenes, polybutadienes, polybutylenes, polyketones, polystyrenes, polysulfones, poly(ethylene terephthalates), polyamides, polyacrylates, PVC, and other polymers used in medical technology.

6. The catheter attachment of claim 1, wherein the non-elastomeric thermoplastic material has a transition temperature above 25° C.

7. The catheter attachment of claim 1, wherein the catheter attachment is a component designed to attach to a catheter external to the patient and remain external to the patient during use.

8. The catheter attachment of claim 1 wherein the catheter attachment is a catheter hub.

9. A process for preparing a catheter attachment according to claim 1 made of plastic, in which pellets of the plastic are brought into intimate contact with the phenoxyphenol (PCPP) to obtain a mixture, followed by melting the mixture and preparing the catheter hub by extrusion or injection molding.

10. The process according to claim 9, wherein said mixture is obtainable by coating the pellets with phenoxyphenol (PCPP).

11. The process according to claim 9, wherein said mixture is obtainable by admixing the pellets with phenoxyphenol (PCPP).

* * * * *